(12) United States Patent
Alvarado et al.

(10) Patent No.: US 11,832,808 B2
(45) Date of Patent: Dec. 5, 2023

(54) INCISIONLESS ENDOLUMINAL GASTRIC TISSUE APPROXIMATION FOR THE TREATMENT OF OBESITY

(71) Applicant: Apollo Endosurgery US, Inc., Austin, TX (US)

(72) Inventors: Alonso Alvarado, Panama (PA); Manoel Galvao, Sao Paulo (BR); Eddie Gomez, Miami, FL (US); Nicole Pena, Santo Domingo (DO); Sohail Shaikh, Clifton, NJ (US); Chris Thompson, Needham, MA (US); Erik Wilson, Houston, TX (US); Natan Zundel, Fort Lauderdale, FL (US); Robert Lulo, Bee Cave, TX (US); Ted Stephens, Spicewood, TX (US)

(73) Assignee: Apollo Endosurgery US, Inc., Austin, TX (US)

( * ) Notice: Subject to any disclaimer, the term of this patent is extended or adjusted under 35 U.S.C. 154(b) by 1108 days.

(21) Appl. No.: 16/397,328

(22) Filed: Apr. 29, 2019

(65) Prior Publication Data
US 2019/0247041 A1 Aug. 15, 2019

Related U.S. Application Data

(62) Division of application No. 14/508,756, filed on Oct. 7, 2014, now abandoned.
(Continued)

(51) Int. Cl.
*A61B 17/04* (2006.01)
*A61B 17/00* (2006.01)
(Continued)

(52) U.S. Cl.
CPC ...... *A61B 17/0469* (2013.01); *A61B 17/0625* (2013.01); *A61B 18/24* (2013.01);
(Continued)

(58) Field of Classification Search
CPC ......... A61F 5/0083; A61B 2017/00818; A61B 2017/0496; A61B 18/24; A61B 90/361
See application file for complete search history.

(56) References Cited

U.S. PATENT DOCUMENTS

4,461,283 A * 7/1984 Doi ...................... A61B 18/245
606/27
8,137,367 B2 * 3/2012 Deem .................. A61B 17/064
606/151
(Continued)

*Primary Examiner* — Sarah W Aleman
(74) *Attorney, Agent, or Firm* — Seager, Tufte & Wickhem, LLP (57) ABSTRACT

An incisionless fully endoscopic method of reducing the capacity of the stomach is provided to surgically treat obesity. The method is directed to endoluminal tissue approximation of a portion of the stomach, including at least a portion of the greater curvature thereof. The method includes a pattern of stitching in which a portion of the stomach is closed off. One stitching pattern causes the lateral portion of the stomach to be drawn to reduce the usable volume of the stomach while maintaining a pathway from the esophagus to the pylorus. As the stitching pattern advances, the fundus is automatically drawn downward so that it may be endoscopically approached for stitching in a facilitated manner. According to another aspect of the invention, another stitching pattern extends from the antrum to the fundus between the anterior and posterior portions of the stomach.

11 Claims, 9 Drawing Sheets

Related U.S. Application Data

(60) Provisional application No. 61/900,049, filed on Nov. 5, 2013.

(51) Int. Cl.
*A61B 17/062* (2006.01)
*A61B 18/24* (2006.01)
*A61B 18/00* (2006.01)
*A61B 90/00* (2016.01)

(52) U.S. Cl.
CPC .............. *A61B 90/361* (2016.02); *A61B 2017/00818* (2013.01); *A61B 2018/00494* (2013.01); *A61B 2018/00589* (2013.01)

(56) References Cited

U.S. PATENT DOCUMENTS

| | | | | |
|---|---|---|---|---|
| 2005/0192599 A1* | 9/2005 | Demarais | ............ | A61F 5/0086 606/151 |
| 2005/0203489 A1* | 9/2005 | Saadat | ............ | A61B 90/39 606/1 |
| 2007/0276408 A1* | 11/2007 | Filipi | ............ | A61B 17/0401 606/139 |

* cited by examiner

INCISIONLESS ENDOLUMINAL GASTRIC TISSUE APPROXIMATION FOR THE TREATMENT OF OBESITY

CROSS-REFERENCE TO RELATED APPLICATION

This application is a divisional of U.S. patent application Ser. No. 14/508,756, filed Oct. 7, 2014 and claims benefit to U.S. Provisional Ser. No. 61/900,049, filed Nov. 5, 2013, which is hereby incorporated by reference herein in its entirety.

BACKGROUND OF THE INVENTION

1. Field of the Invention

The present invention relates to surgical procedures. More particularly, the invention relates to a method of effecting stomach reduction to treat obesity. Specifically, the method is directed to an endoscopic incisionless procedure to reduce the internal volume of the stomach without relocating the small intestines.

2. State of the Art

The condition of obesity means an individual has too much body fat and also that an individual's weight is higher than what is considered to be healthy for their height. Biology plays a big role in why some people become obese, but not getting enough exercise, eating more food than the body can use, and drinking too much alcohol also contributes to people becoming obese. Obesity is a major health threat because excess weight puts more stress on every part of the body and puts people at risk of several health problems, such as diabetes, heart disease, and stroke.

For some people, lifestyle changes like maintaining a healthy diet and exercising regularly can help them drop body fat and stop being obese. For others though, it can be extremely difficult to lose body fat and consistently maintain weight loss. Medications for losing weight are available on the market, but some can have serious side effects and may not actually be effective. For obese individuals who can not lower their amount of body fat through lifestyle changes or medications, various surgical options have become available.

Gastric bypass surgery was the first commonly practiced procedure performed to make the stomach smaller. The procedure involves stapling portions of the stomach wall together and then relocating a small part of the small intestine to the newly formed stomach pouch. By reducing the size of the stomach, the stomach holds less food, the individual obtains a sensation of fullness quicker, fewer calories are eaten, fewer calories are absorbed, and weight loss results. However, there are downsides to the procedure. The procedure is an open surgical procedure which has its own risks, including the potential for complications and infection, and can have an extensive post-surgical recovery period. The procedure is also relatively complicated requiring a reconfiguration of the small intestines. Also, over time the staples can release allowing the stomach to re-enlarge, rendering the procedure less effective.

Another procedure is the 'gastric banding' procedure, primarily with the LAP-BAND® system, in which an inflatable band is inserted through the abdomen and about the stomach in either a laparoscopic procedure. The band is wrapped around the upper part of the stomach to form a stoma, or ring. Attached to the ring is a thin tube leading to an access port that is implanted under the skin. A balloon attached to the band contacts the stomach and can be inflated (or deflated) with saline via the access port using a needle. Adding saline tightens the stoma about the stomach to effect an earlier sensation of satiety. If the band is too tight, saline can be withdrawn. An advantage of the gastric banding is that it can be performed in a minimally invasive manner with small laparoscopic incisions into the abdomen with consequent reduced recovery time, and that no reconfiguration of the small intestines is required. Nevertheless, the procedure still requires incisions, infection can result, and can the recovery can be uncomfortable. In addition, the patient is left with a permanent port just under their skin which can be undesirable to some.

These types of procedures, when all goes well, can be effective, but as stated come with the risks associated with open or laparoscopic surgery, and for that reason they are only prescribed in cases of extreme obesity.

A more recent procedure called Primary Endoluminal Obesity Surgery (POSE) is carried out endoscopically via the gastroesophageal tract into the stomach, completely without incisions. The procedure includes the creation of a series of plications solely in the gastric fundus that are maintained with respective clips. With the creation of each plication, two locations of stomach tissue are gathered, drawn together, and secured, with the result that the stomach capacity is reduced. As a consequence, the patient has somewhat diminished hunger cravings. The POSE procedure theoretically offers an advantages over the other surgeries requiring an incision: less pain, decreased risk of infection, no external scarring, faster recovery, shorter hospital stay to name a few. However, the amount of stomach capacity reduction that can be practically be achieved with POSE is controverted. Acting solely on the fundus and in the manner practiced, it is thought to be significantly less that the seventy percent reduction in capacity claimed by the developers of the procedure; it may be more realistic to anticipate a thirty percent reduction in stomach capacity with the POSE procedure. Moreover, working endoscopically to create clipped plications in the fundus is difficult, as the endoscope and tools working through the channels of the endoscope must be operated in a retroflexed manner, which makes access to the fundus, maneuvering of the instruments, and reducing the fundus challenging.

SUMMARY OF THE INVENTION

An incisionless fully endoscopic method of reducing the capacity of the stomach is provided to surgically treat obesity. Broadly, the method is directed to endoluminal tissue approximation of a portion of the stomach, including at least a portion of the greater curvature thereof. In one aspect of the invention, the method is directed to a pattern of endoscopic stitching in which a significant portion of the stomach is closed off. According to one aspect of the invention, the anterior and posterior walls of the stomach are marked along the greater curve of the stomach to create guidelines for sutures. The guideline may be made with a coagulator, dye or other marking device or substance. The stitching pattern subsequently proceeds along the guidelines.

According to yet another aspect of the invention, one stitching pattern causes the lateral portion of the stomach; i.e., extending along the greater curve of the stomach to be drawn in or collapsed inward to thereby remove such portion of the greater curve from the usable volume of the stomach while maintaining a usable pathway from the esophagus to the pylorus. The pattern is initiated below the fundus, and as the pattern advances, the fundus is automatically drawn downward so that it may be endoscopically approached for stitching without necessitating any or any significant retroflex of the endoscope and stitching instruments used therewith. In this manner, the method provides a procedure in which access to the anatomy being sutured is facilitated relative to prior art incisionless stomach reduction procedures. According to another aspect of the invention, another stitching pattern extends from the antrum (lower portion) to the fundus (upper portion) between the anterior and posterior portions of the stomach.

More particularly, a preferred method includes, for each of a plurality of vertically displaced locations along the greater curve of the stomach, suturing three points about the stomach together and cinching the three points toward each other. The three points are located at an anterior side, a posterior side, and a lateral side. The three points can be attached in a point-to-point arrangement; i.e., anterior-to-posterior, posterior-to-lateral, and lateral-to-anterior, and when each of the point-to-point locations is cinched the greater curve of the stomach collapses inward to eliminate the volume of such portion of the stomach at the cinched locations.

More preferably, the three points are sutured in a continuous process in which each of the anterior, posterior and lateral points are coupled together with a single suture and then cinched. A helical suturing pattern may be used in which an arrangement of vertically displaced sets of anterior, posterior and lateral points are coupled together with a single suture and cinched to draw the greater curve of the stomach inward upon itself and reduce the stomach volume thereat. It is anticipated that five to seven such helical suturing patterns, each with a separate suture, are used to fully draw in and collapse the greater curve of the stomach.

In accord with a preferred aspect of the invention, the helical suturing pattern starts at or adjacent the antrum; subsequently, the helical suturing pattern continues to the body of the stomach. Alternatively, the stomach can be helically sutured in order: antrum, then fundus, and finally body. Once the antrum and/or body are sutured and cinched, the cinching causes the fundus to be automatically drawn downward to effectively shorten the length of the fundus. As the shape of the fundus is altered, it can be approached for suturing without retroflexing the endoscope or other instruments. This greatly facilitates the procedure.

After the greater curve of the stomach has been drawn into a collapsed configuration from the antrum to the fundus to effectively close off a significant volume of the stomach, the anatomical revision is secured by running a vertical pattern of suture stitches between the anterior and posterior sides of the stomach at locations medial of the previously drawn in and secured tissue; i.e., along the lesser curve, to further seal off the cinched portion of the stomach and ensure a patent pathway between the esophagus and the pylorus.

The resulting stomach reduction procedure provides a seventy to seventy-five percent reduction in available stomach volume, greater than any other incisionless procedure. Also, because it is incisionless, it is safer to patients and offers an easier recovery. Moreover, as an incisionless procedure, it is easier for the surgeon to effectively perform than other incisionless procedures, providing more direct access to the fundus for reduction.

DETAILED DESCRIPTION OF THE PREFERRED EMBODIMENTS

Figure 1A:
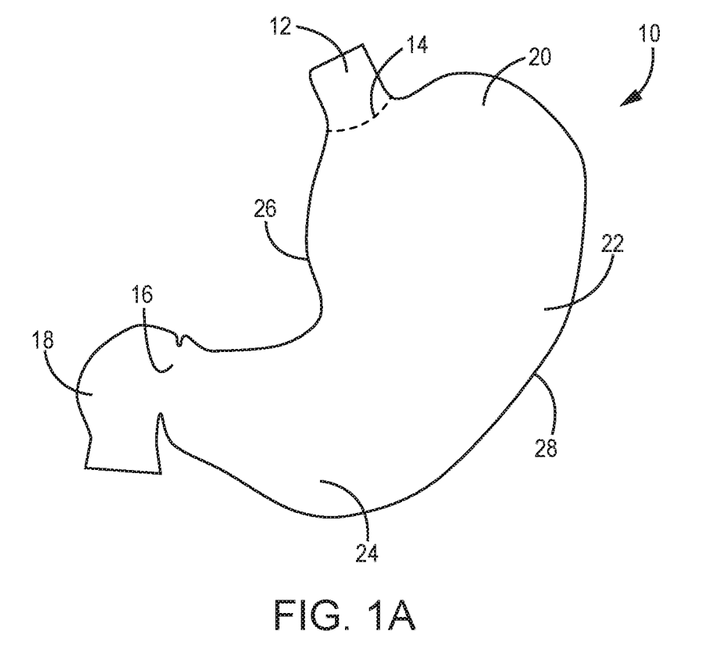
FIG. 1A is a schematic illustration of the stomach.

Referring now to FIG. 1A, an illustration of the stomach 10 with standard reference locations are shown. The gastroesophageal junction 14 at the upper end of the stomach is joined to the lower end of the esophagus 12, and the pylorus 16 defined at the lower end of the stomach is joined to the duodendum 18 of the small intestines. The upper portion of the stomach is the fundus 20 and extends vertically above of the gastroesophageal junction 14, the central portion is the body 22, and the lower portion of the stomach is the antrum 24. The medial side of the stomach forms a concave curve referred to as the lesser curvature (or curve) 26, whereas the lateral side of the stomach forms a larger convex curve referred to as the greater curvature (or curve) 28.

Figure 1B:
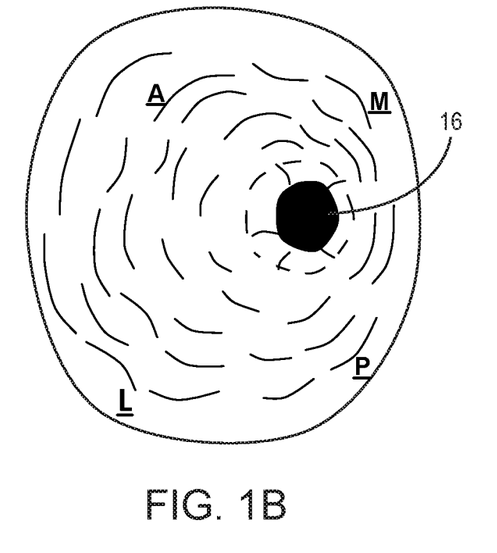
FIG. 1B is a schematic illustration from inside the stomach, viewed from the fundus toward the pylorus.

Turning now to FIG. 1B, an interior of the stomach is shown, viewed from the fundus (top) toward the pylorus (bottom). In addition, the anterior (A), posterior (P), lateral (L), and medial (M) sides of the stomach are identified. The lateral side (L) extends with the greater curvature 28 of the stomach, and the opposing medial side (M) extends with the lesser curvature 26 (see FIG. 1A).

In accord with a general description of the method of the invention, described in more detail below, instruments are provided and used to endoscopically reduce the volume of the stomach by first reducing the volume of the body 22 and/or the antrum 24 of the stomach, and then reducing the volume of the fundus 20 of the stomach. The term 'endoscopically', as used herein, means through or with the aid of an endoscope in which the instruments acting to reduce the stomach volume are inserted through a natural orifice, namely the gastroesophageal pathway, preferably without incision to either the dermal or internal tissues of a patient in order to effect for passage of the required instruments. Specifically, it is recognized that suturing does not effect an incision in tissue. In addition, the term 'vertically' as used herein is in reference to the upper and lower portions of the gastrointestinal tract in relation to the passage of nutrients, i.e., with the upper end (fundus) located vertically above the lower end (pylorus) regardless of the orientation of the patient.

Generally, an endoscopic method of reducing the capacity of the stomach is provided to surgically treat obesity. The reduction of the stomach is performed by endoscopically drawing together and approximating preferably three peripherally displaced locations of the stomach wall (at the anterior side (A), posterior side (P), and lateral side (L)), and cinching such locations into approximation. This process is carried out at several vertically displaced portions of the stomach, preferably including at each of the antrum 24, the body 22, and the fundus 20. Once the peripherally and vertically displaced locations of the stomach 10 are endoscopically approximated to result in reducing the lateral side volume of the stomach (i.e., preferably covering substantially all of the antrum, the body, and the fundus of the stomach), preferably a vertical row of stitches is endoscopically placed between the anterior and posterior sides of the stomach to seal off the previously drawn together portions of the stomach to result in a significantly re-sized stomach volume and patent pathway between the gastroesophageal junction 14 and the pylorus 16.

More particularly, the method requires a pattern of endoscopic suture stitching in which a significant portion of the stomach is closed off with stitches extending from the antrum 24 to the fundus 20 between the anterior (A) and posterior (P) sides of the stomach. The suture 54 (shown in FIG. 3) is preferably any suitable suture material, e.g., polymeric and/or metal, in the form of a filament, braid or cable. After generation of the suture pattern, the suture is cinched to cause the lateral side (L) of the stomach; i.e., that portion extending along the greater curvature 28 of the stomach, to be drawn in or collapsed inward (toward the medial side (M)) to thereby remove such portion of the greater curvature from the usable volume of the stomach while maintaining a pathway from the esophagus 12 to the pylorus 16.

Figure 2A:
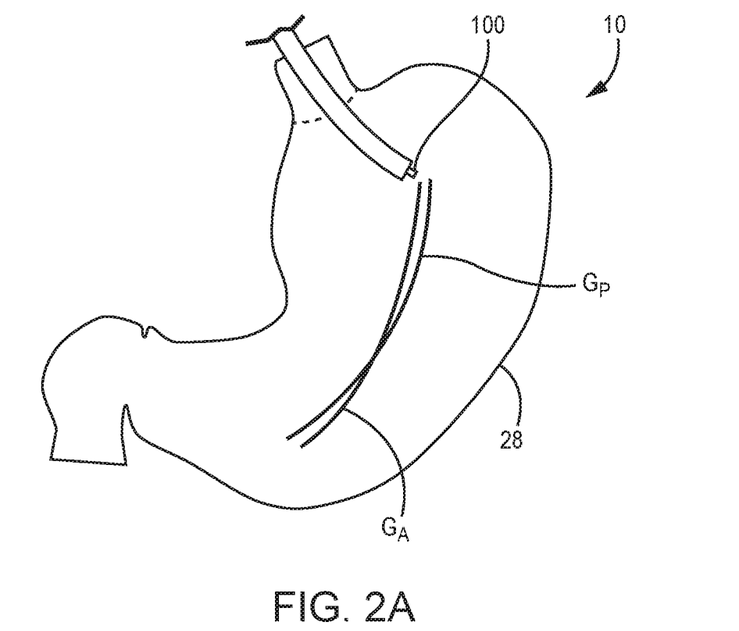
FIG. 2A is a schematic illustration of the stomach, shown with marking instrument inserted therein to provide guidemarks parallel to the greater curvature.
Figure 2B:
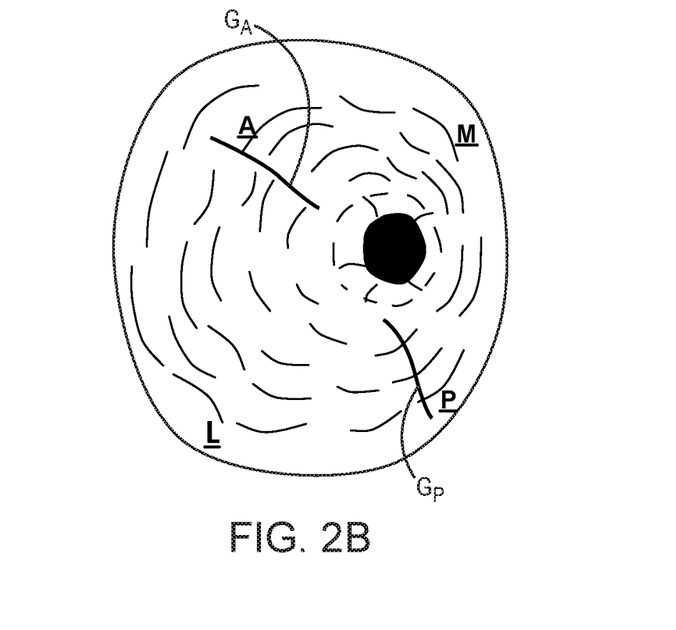
FIG. 2B is a schematic illustration from inside the stomach, showing anterior and posterior guidemarks parallel to the greater curvature.

Referring to FIGS. 2A and 2B, one preferred method includes marking the anterior and posterior sides A, P of the stomach 10 along the greater curvature 28 of the stomach to create guidelines $G_A$, $G_P$ for subsequent sutures. This is particularly helpful, as the guidelines provide a reference line or reference axes as the stomach tissue is cinched, as discussed below. The guidelines may be marked with a coagulator, dye or other marking device or substance. One preferred marking device 100 is the argon plasma coagulator, which can be used to create a continuous guideline on the stomach lining. Another device that can be used is a needle knife and dye, which can generate dotted-line or continuous guidelines. The stitching pattern subsequently proceeds along or relative to the guidelines $G_A$, $G_P$. The guidelines, while preferred, are not essential to the practice of the method.

After marking the guidelines, for each of a plurality of vertically displaced locations along the greater curve of the stomach, three displaced locations (suture 'points') along the stomach wall are sutured together and then cinched toward each other. The three points are located at an anterior side, a posterior side, and a lateral side. The three points can be attached in a point-to-point arrangement; i.e., anterior-to-posterior, posterior-to-lateral, and lateral-to-anterior, and when each of the point-to-point locations is respectively cinched, the greater curve of the stomach collapses inward to eliminate the volume of such portion of the stomach at the cinched locations. The process would then be repeated at vertically displaced locations, preferably proceeding from the antrum toward the fundus.

Figure 3:
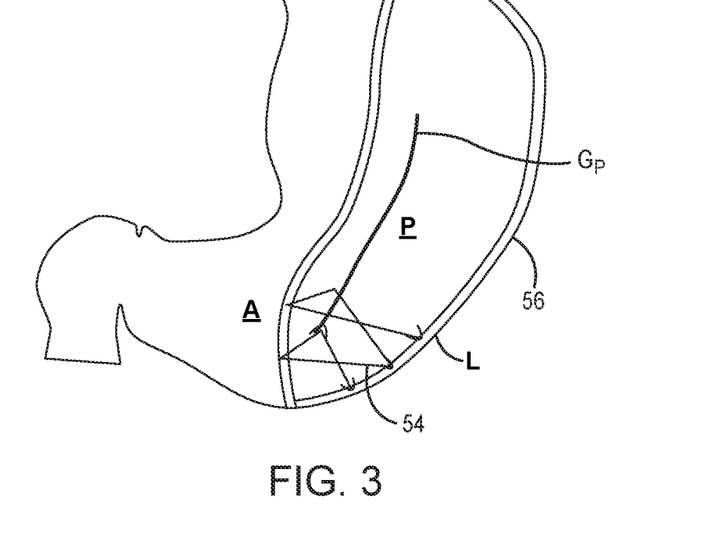
FIG. 3 is a partial section view of stomach, illustrating placement of a first suture of a first suture stitching pattern according to the method of the invention.
Figure 5:
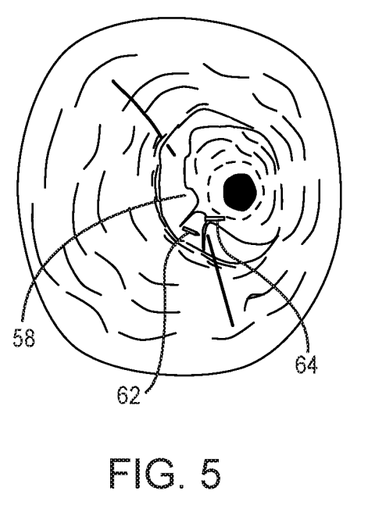
FIG. 5 is a view similar to FIG. 4, showing the first suture cinched.
Figure 6:
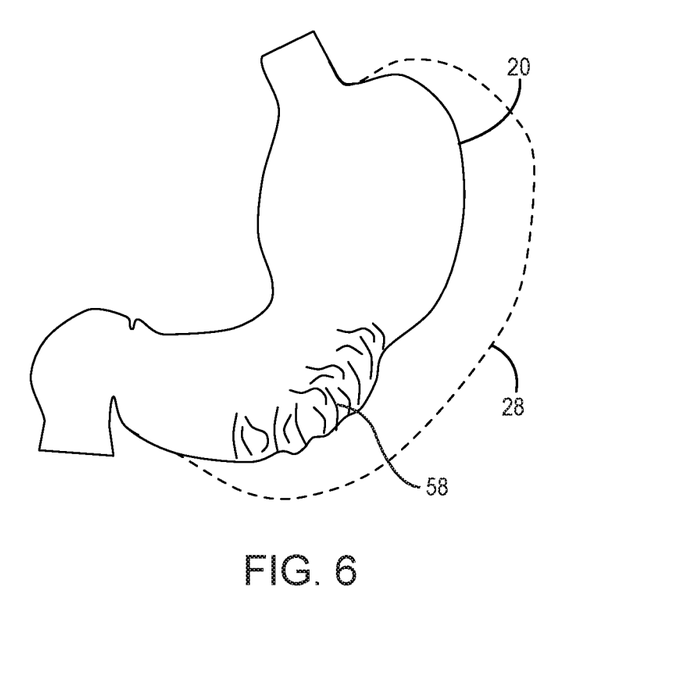
FIG. 6 is a schematic side view of stomach illustrating the cinched antrum as a result of the first cinched suture and the corresponding reconfiguration of the greater curvature of the stomach.

Turning to FIG. 3, in one preferred procedure, the three points (A, P, L) are sutured in a continuous process in which each of the anterior, posterior and lateral points are coupled together with a single suture. More preferably, a helical suturing pattern is provided in which an arrangement of vertically displaced sets of anterior, posterior and lateral points, e.g., 50A, 50P, 50L and 52A, 52P, 52L are coupled together with a single suture 54. Each set preferably includes five to seven points of engagement about anterior, posterior, and lateral sides of the stomach wall 56, engaged with the common suture 54. Referring to FIGS. 5 and 6, the suture 54 is then cinched to draw anterior, posterior, and laterals sides together into approximation, and consequently the greater curve 28 of the stomach inward upon itself into a collapsed configuration 58. This reduces the stomach volume in the area engaged by the suture (FIG. 5). The suture 54 is retained to the stomach tissue 56 preferably with a retained needle 62 that operates as a tissue tag at one end of the suture 54, and an applied cinch 64 at the opposite end of the suture, discussed in more detail below.

Figure 4:
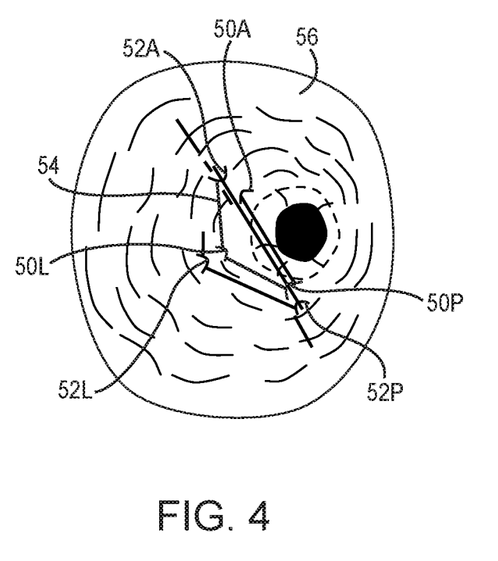
FIG. 4 is a view similar to FIG. 2A, showing the first suture of the first suture stitching pattern as FIG. 3.

As shown in FIGS. 3 through 5, the suturing and subsequent cinching starts below the fundus, e.g., at or adjacent the antrum. Referring to FIG. 6, as the anterior, posterior, and lateral sides of the stomach are cinched together with the suture starting from a relatively vertically low location in the stomach (near the antrum), such cinching causes the fundus 20 to be automatically drawn downward to effectively shorten the length of the fundus, comparing the reshaped fundus 20 to the original configuration in dotted lines. As the shape of the fundus 20 is altered, the fundus can be subsequently approached for suturing without retroflexing the endoscope or other instruments required for the suturing process. In this manner, the method facilitates access to the anatomy, and particularly the fundus, relative to prior art incisionless stomach reduction procedures. It is anticipated that three to seven such helical suturing patterns, each with a separate suture, are used to fully draw in and collapse the greater curve of the stomach.

Figure 7:
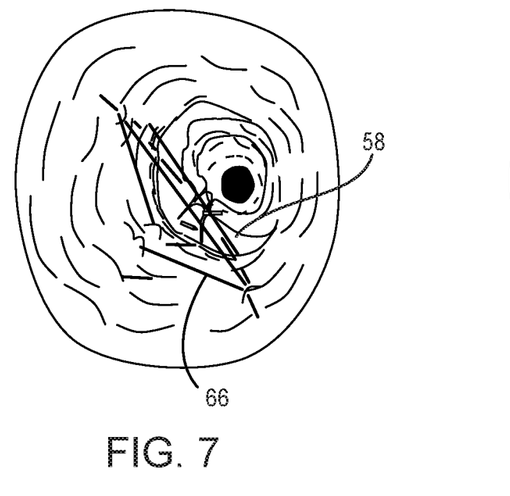
FIG. 7 is a view similar to FIG. 5, illustrating a second suture of a first suture stitching pattern, and the first suture cinched.
Figure 8:
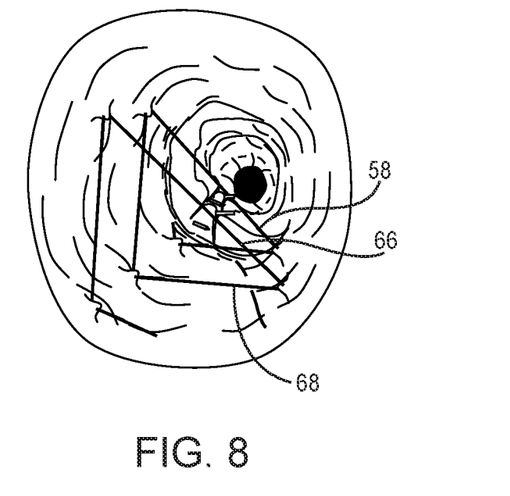
FIG. 8 is a view similar to FIG. 7, illustrating a third suture of a first suture stitching pattern, and the first and second sutures cinched.
Figure 9:
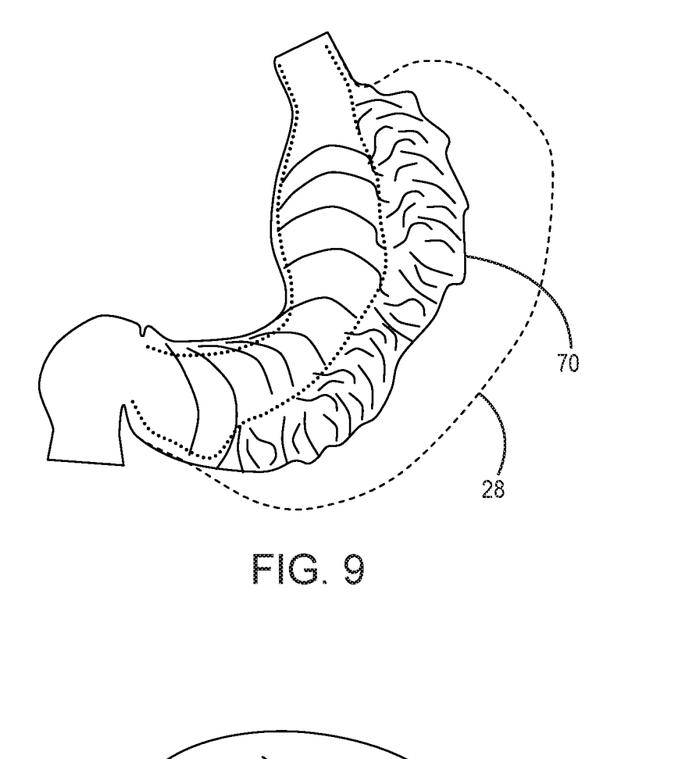
FIG. 9 is a schematic side view of stomach illustrating the cinched antrum, body, and fundus, and the corresponding reconfiguration of the greater curvature of the stomach.

Thus, turning to FIG. 7, a second preferably helical pattern of suture 66 is shown vertically above the lower collapsed stomach tissue 58, e.g., at or near the body 22 of the stomach. When suture 66 is cinched, the anterior, posterior, and lateral sides of the stomach wall are drawn into approximation at and adjacent the points of suture engagement. In FIG. 8, a third preferably helical pattern of suture 68 is shown vertically above both the lower cinched and collapsed stomach tissue and stomach tissue cinched and collapsed via the second suture pattern 66. In this example, the third pattern is shown inserted through the drawn down fundus 20. Additional suturing in a vertically displaced manner from those shown, but preferably in the pattern described, is repeated as necessary to collapse the greater curvature 28 from the antrum to the fundus to the configuration 70 shown in FIG. 9.

Figure 10:
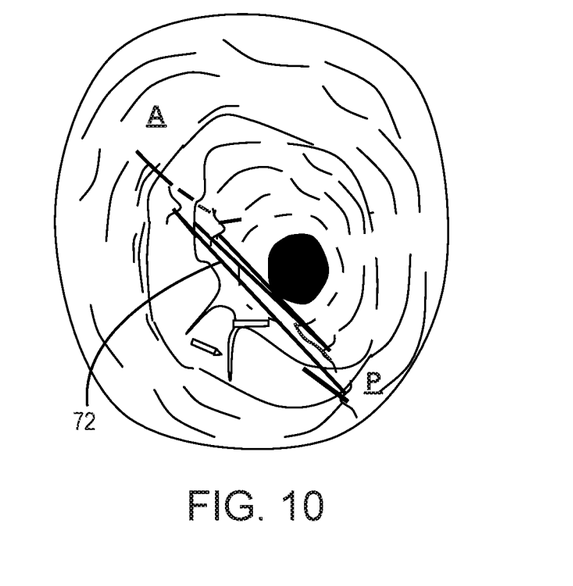
FIG. 10 is a schematic illustration from within the stomach, after the first suture pattern has been completed, and showing placement of the second suture pattern in the anterior-posterior direction.
Figure 11:
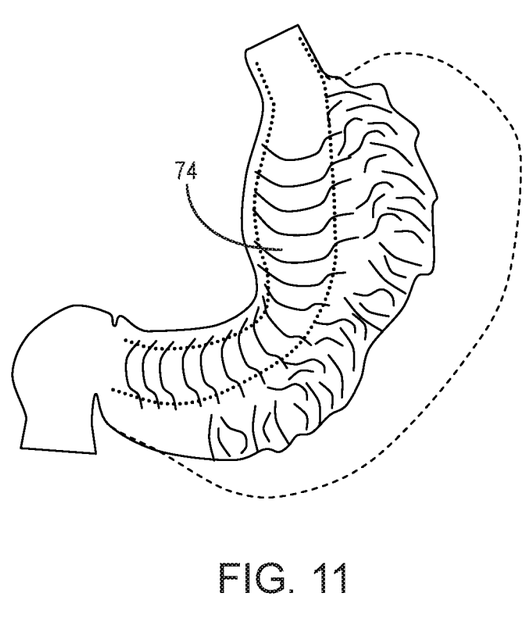
FIG. 11 is a schematic side view of the stomach illustrating the cinched sutures of both of the first and second suture patterns.

Turning to FIG. 10, after the greater curvature 28 is collapsed, in accord with another preferred aspect of the invention, a running row of a suture stitches is advanced from the antrum 24 to the fundus 20 along the collapsed portion of the stomach. It is preferred that a continuous vertical row of stiches be provided through the stomach alternating in the anterior-posterior direction; e.g., by engaging the anterior side of the stomach wall with a suture 72, then passing the suture through the posterior side at a vertically higher location, then passing the suture back through the anterior side at a vertically higher location than engaged at the posterior, and so on. After the suture 72 is threaded through several locations in the alternating anterior-posterior arrangement, the suture is cinched to draw the anterior and posterior sides of the stomach wall together to define a relatively smooth passage 74 between the lesser curvature and the now stitched tissue, as shown in FIG. 11. The passage 74 preferably excludes the approximation of the previously stitched anterior, posterior, and lateral sides. One or more suture threads can be used to carry out the vertical row of sutures. As an alternate embodiment, the anterior-posterior row of suture stitches may be comprised of several vertically displaced and substantially completely discrete point-to-point anterior-posterior suture stiches to effect the vertical row. Once the row is complete, several advantages are provided. The row of stitches secures the prior reshaping of the stomach. The row of stiches further reduces the size of the stomach. The row of stitches provides a smoother and more well-defined passage 74 from the upper to the lower ends of the stomach.

Figure 12:
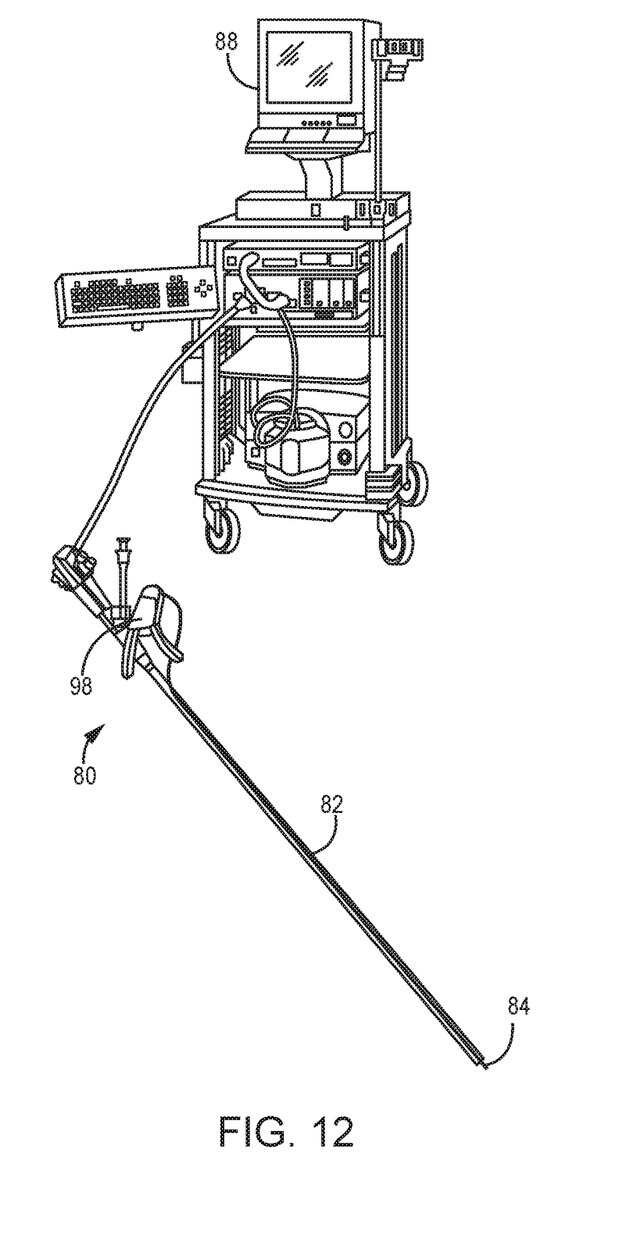
FIG. 12 is a perspective view of an endoscopic suturing system.
Figure 13:
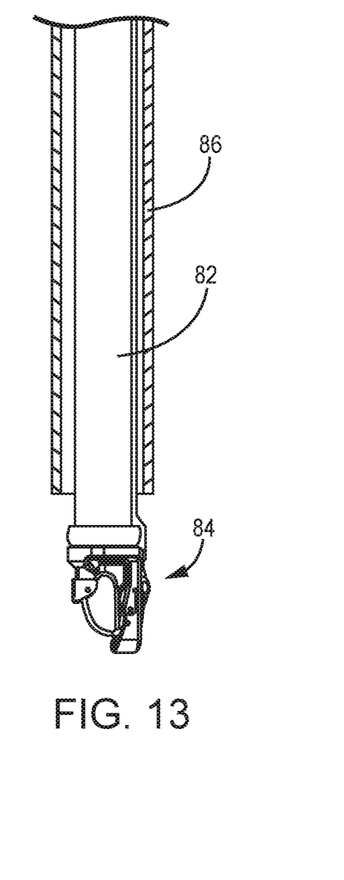
FIG. 13 is a broken partial section view of a distal end of the endoscopic suturing system extending through the distal end of an overtube.
Figure 14:
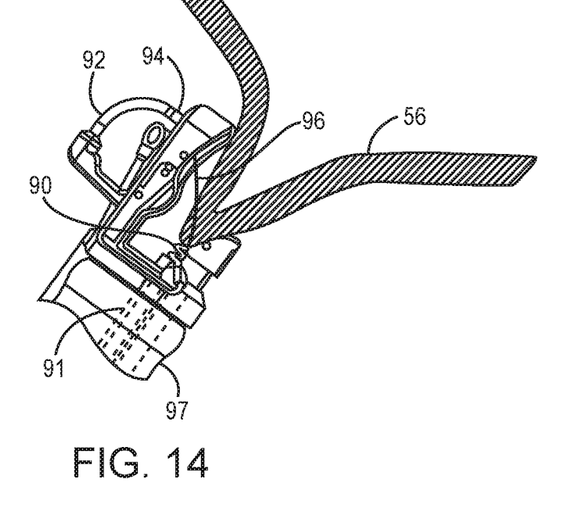
FIGS. 14 through 17 illustrate operation of the endoscopic suturing system to endoluminally place stitches of suture through stomach tissue.
Figure 15:
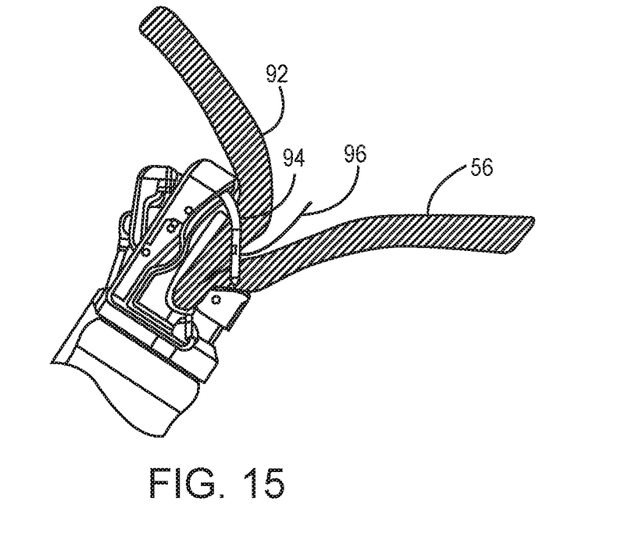
Figure 16:
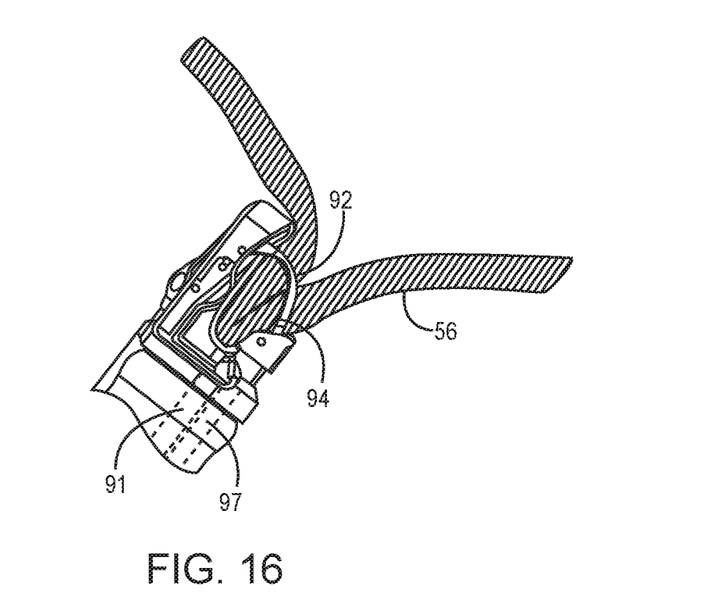
Figure 17:
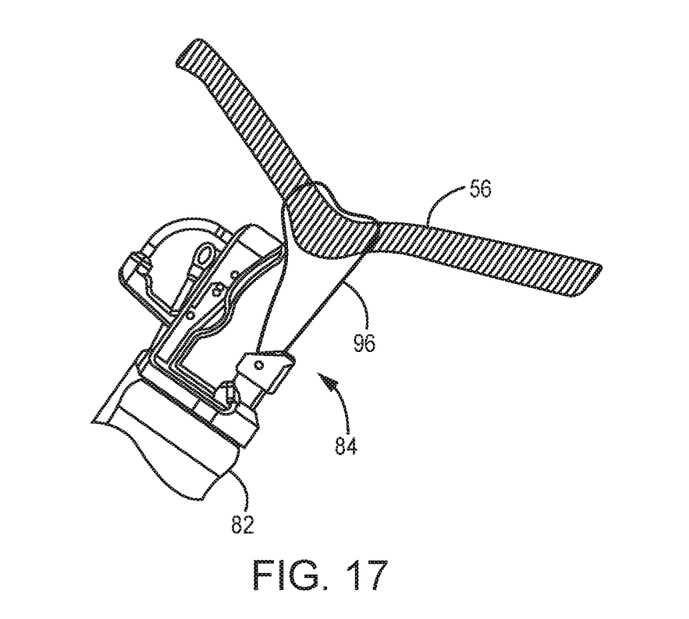

In order to endoscopically suture the stomach as described above, an endoscope is advanced through the esophagus and into the stomach. The endoscope is provided with tools to effect endoluminal stitching of sutures through the stomach wall. Co-owned US Pub. No. 2012/0157765, which is hereby incorporated by reference herein in its entirety, discloses a suitable and preferred endoscopic suturing system 80, shown at FIGS. 12 and 13, which is capable of the effecting the suturing of the stomach wall together in accord with the method described above. The endoscopic suturing system 80 includes a steerable endoscope 82 and an endoscope-mounted needle passing system 84, which are together preferably passed through the gastroesophageal tract and into the stomach through an overtube 86. A display 88 is provided for viewing the images from the endoscope. The system 80 operates in conjunction with instruments passed through one or more of the working channels of the endoscope. More particularly, turning to FIG. 14, the system 80 allows the engagement of stomach tissue 56 (e.g., at the lateral side of the stomach) using a tissue grasper 90 extending through a first working channel 91 of the endoscope 82, a rotatable arm 92 mounted relative to the end of the endoscope, the rotatable arm 92 releasably engaging a needle 94 having a length of suture 96 fixed relative thereto. A control handle 98 (FIG. 12) is operable to rotate the arm 92 from an open configuration to an intermediate configuration (FIG. 15) to a closed configuration (FIG. 16) so as to pass the needle 94 and suture 96 through the engaged tissue 56. A needle capture device (not shown) extends within a second working channel 97 of the endoscope 82 and, with the arm 92 and needle 94 in the position shown in FIG. 16, is operated to capture the needle 94 after it has been passed through the engaged tissue 56. The handle 98 is then operated to open the rotatable arm 92, resulting in release of the needle 94 from the rotatable arm 92, and the needle 94 is retained at the capture device within the working channel of the endoscope. Referring to FIG. 17, the endoscope 82 can then be retracted relative to the tissue 56 to pull the suture 96 through the tissue, and once the distal end of the endoscope-mounted needle passing system 94 is free of the tissue, the rotatable arm 42 is rotated toward the needle capture device to re-engage the needle 44 with the arm 42 (not shown). The endoscope is then maneuvered to a different tissue location (e.g., at the posterior side of the stomach) and the process is repeated at the next location. The suture process continues at all desired locations (i.e., continuing to the anterior side of the stomach) for the particular length of suture.

Once the suturing at the respective locations for a particular suture is complete, the suture is then cinched and locked in the cinched configuration with a cinch. In accord with one preferred cinch applying system and method, described in co-owned US Pub. No. 2012/0158023, which is hereby incorporated by reference herein in its entirety, a single-use suture cinch system is provided which is advanceable through a working channel of the endoscope to apply a suture cinch to the suture adjacent the inner stomach tissue to lock the suture relative to the tissue and retain the suture in the cinched configuration. In accord with another preferred cinching system and method, described in co-owned U.S. Provisional App. No. 61/777,607, which is hereby incorporated by reference herein in its entirety, a reloadable cinch system can be used to apply cinches to one or more strands of suture to retain the sutures in respective cinched configurations. All of the above can be used endoscopically through a natural orifice, preferably under visualization of an endoscope. The structure and operation of the preferred endoscopic suturing system and cinch applying systems, as well as various alternate embodiments thereof, are described in greater detail in the referenced publications. It is further appreciated that other endoscopic suturing systems, and suture cinch applying systems, including other peripheral components used in association therewith, can be used to effect the method described herein, provided that they are suitable (for example, but not by way of limitation, in terms of safety and capability) for the tasks required.

The resulting stomach reduction procedure provides a seventy to seventy-five percent reduction in available stomach volume, greater than any other incisionless procedure. Also, because it is incisionless, it is safer to patients and offers an easier recovery. Moreover, as an incisionless procedure, it is easier for the surgeon to effectively perform than other incisionless procedures, providing more direct access to the fundus for reduction.

There have been described and illustrated herein several embodiments of an incisionless endoluminal method of tissue approximation within the stomach to reduce the stomach volume. While particular embodiments of the invention have been described, it is not intended that the invention be limited thereto, as it is intended that the invention be as broad in scope as the art will allow and that the specification be read likewise. Thus, while particular systems, instruments, and devices have been disclosed to position the sutures within the stomach tissue, and cinch and secure the sutures for tissue approximation, it will be appreciated that other system, instruments, and device can be used as well. In addition, while a particular preferred number of stitches has been disclosed, it is appreciated that a fewer or more sutures can be used to draw the tissue into approximation, including a single suture extending from near the pylorus to the upper end of the stomach, and that such suture can be cinched in stages. Also, while suturing in the described pattern is a preferred method for effecting the described tissue approximation of the anterior, posterior and lateral sides of the stomach in order to draw in the greater curvature, as well as the running vertical approximation of the anterior and posterior sides after the greater curvature is drawn in, it is recognized that the method is not limited to the use of suture, and that other tissue securing elements can be used. It will therefore be appreciated by those skilled in the art that yet other modifications could be made to the provided invention without deviating from its spirit and scope as claimed.

What is claimed is:

1. A method of treating obesity in a patient, the patient having a stomach having an antrum, a central body, and a fundus, the stomach having a stomach wall with anterior, posterior, lateral and medial sides, the method comprising:
   a) providing an endoscopic tissue suturing system;
   b) endoluminally passing the endoscopic tissue suturing system through a natural orifice into the stomach;
   c) using the endoscopic tissue suturing system to advance a first suture through first locations through the anterior, posterior, and lateral sides of the stomach wall below the fundus;
   d) first cinching the first suture to draw inward into approximation the anterior, posterior, and lateral sides at the first locations;
   e) then using the endoscopic tissue suturing system to advance a second suture through second locations through the anterior, posterior, and lateral sides of the stomach wall vertically displaced above the first locations, wherein the second locations are located within the fundus; and
   f) second cinching the second suture to draw inward into approximation the anterior, posterior, and lateral sides at the second locations.

2. The method of claim 1, wherein the first suture is advanced in a helical pattern about the stomach wall.

3. The method of claim 2, wherein the second suture is advanced in a helical pattern about the stomach wall.

4. The method of claim 1, wherein:
   said first cinching the first suture includes applying a first cinch to the first suture to secure the first suture in a cinched configuration relative to the stomach wall below the fundus; and
   said second cinching the second suture includes applying a second cinch to the second suture to secure the second suture in a cinched configuration relative to the stomach wall.

5. The method of claim 1, further comprising:
   using the endoscopic tissue suturing system to advance a third suture between the anterior and posterior sides of the stomach in an alternating pattern at vertical displaced locations; and
   cinching said third suture to form a passage within the stomach that exclude the approximation of the anterior, posterior, and lateral sides at the first and second locations.

6. The method of claim 1, further comprising before advancing the first suture through the anterior, posterior, and lateral sides of the stomach wall, marking a guideline along the stomach wall.

7. The method of claim 6, wherein a separate guideline is marked on each of the anterior and posterior sides of the interior stomach wall.

8. The method of claim 6, wherein the guideline is marked with a laser coagulator.

9. The method of claim 1, wherein the first cinching draws the anterior, posterior, and lateral sides into contact at the first locations.

10. The method of claim 9, wherein the second cinching draws the anterior, posterior, and lateral sides into contact at the second locations.

11. The method of claim 1, wherein the first cinching comprises causing the fundus to be drawn downward to effectively shorten the length of the fundus.

* * * * *